(12) United States Patent
Lessig et al.

(10) Patent No.: US 8,523,858 B2
(45) Date of Patent: Sep. 3, 2013

(54) ADJUSTABLE FIXATION CLAMP AND METHOD

(75) Inventors: Richard K Lessig, Phoenixville, PA (US); Robert J. Chilton, III, Aston, PA (US)

(73) Assignee: Depuy Synthes Products, LLC, Raynham, MA (US)

( * ) Notice: Subject to any disclaimer, the term of this patent is extended or adjusted under 35 U.S.C. 154(b) by 1411 days.

(21) Appl. No.: 11/159,064

(22) Filed: Jun. 21, 2005

(65) Prior Publication Data
US 2006/0287652 A1    Dec. 21, 2006

(51) Int. Cl.
*A61B 17/60*    (2006.01)
(52) U.S. Cl.
USPC ............. 606/54; 606/324; 24/335; 24/135 R; 269/6; 269/71
(58) Field of Classification Search
USPC .................. 606/54, 277, 324; 403/373, 385, 403/389, 391, 393, 396, 400; 24/335, 135 R, 24/459, 525, 569; 29/243.55; 269/3, 6, 95, 269/71
See application file for complete search history.

(56) References Cited

U.S. PATENT DOCUMENTS

| 24,303 | A | * | 6/1859 | Herald et al. ................ | 172/713 |
| 209,945 | A | | 11/1878 | Tompkins | |
| 369,143 | A | | 8/1887 | White | |
| 429,357 | A | * | 6/1890 | McBee ........................ | 248/68.1 |
| 505,215 | A | * | 9/1893 | Buffinton .................... | 248/67.5 |
| 508,687 | A | * | 11/1893 | Duggan ....................... | 174/157 |
| 897,903 | A | * | 9/1908 | Kennedy ...................... | 403/216 |
| 902,040 | A | * | 10/1908 | Wyckoff ....................... | 403/391 |
| 1,190,502 | A | | 7/1916 | Anderson | |
| 1,230,215 | A | * | 6/1917 | Pleister ......................... | 403/391 |
| 1,388,692 | A | * | 8/1921 | Blaeser ......................... | 403/391 |
| 1,635,200 | A | * | 7/1927 | Zilliox ......................... | 439/781 |
| 1,834,495 | A | * | 12/1931 | Morse ........................... | 403/216 |

(Continued)

FOREIGN PATENT DOCUMENTS

DE    3539616    5/1986
DE    3805178    8/1989

(Continued)

*Primary Examiner* — Eduardo C Robert
*Assistant Examiner* — Julianna N Harvey
(74) *Attorney, Agent, or Firm* — Fay Kaplun & Marcin, LLP

(57) ABSTRACT

An adjustable fixation clamp having first and second clamp assemblies positioned about a shaft. The clamp assemblies may each have a pair of vise plates. Each pair of vise plates may define at least two receiving portions and insertion portions intersecting the receiving portions. The receiving portions of one clamp assembly may receive at least two fixation components such as screws, pins or wires. The receiving portions of the other clamp assembly may receive at least one connector such as a rod, bar and/or ring. A biasing structure may be positioned between the first and second clamp assemblies and may allow for the fixation components to be snapped into the receiving portions through the insertion portions. Two or more adjustable fixation clamps may be used to form an external fixation system. At least two screws, pins or wires may be inserted into bone and one of the clamp assemblies may be attached thereto. A guide may be used for insertion of screws, pins or wires into bone. The other clamp assembly may be connected to a rod, bar or ring. Thereafter, the clamp assemblies may be oriented relative to each other and locked in place.

16 Claims, 8 Drawing Sheets

(56) References Cited

U.S. PATENT DOCUMENTS

| | | | |
|---|---|---|---|
| 1,950,635 A | | 3/1934 | Steinmayer |
| 2,081,047 A | * | 5/1937 | Basch ................. 204/196.17 |
| 2,621,384 A | * | 12/1952 | Slaughter ................. 248/137 |
| 2,712,167 A | * | 7/1955 | Blanchard ................. 24/569 |
| 2,767,003 A | | 10/1956 | Gilmont |
| 2,821,762 A | * | 2/1958 | Foose ................. 24/459 |
| 3,012,091 A | * | 12/1961 | Schiffmann ................. 174/94 S |
| 3,026,497 A | * | 3/1962 | Myers et al. ................. 439/781 |
| 3,055,398 A | * | 9/1962 | Tunnessen ................. 248/49 |
| 3,146,982 A | * | 9/1964 | Budnick ................. 248/68.1 |
| 3,188,602 A | * | 6/1965 | Toedtman et al. ................. 439/479 |
| 3,199,062 A | * | 8/1965 | Wantz, Jr. ................. 439/479 |
| 3,248,684 A | * | 4/1966 | Hubbard et al. ................. 439/431 |
| 3,553,351 A | * | 1/1971 | Lindsey ................. 174/169 |
| 4,114,846 A | * | 9/1978 | Petersen ................. 248/68.1 |
| 4,131,257 A | * | 12/1978 | Sterling ................. 248/67.5 |
| 4,142,813 A | * | 3/1979 | Laborde ................. 403/391 |
| 4,600,000 A | | 7/1986 | Edwards |
| 4,620,533 A | | 11/1986 | Mears |
| 4,662,365 A | | 5/1987 | Gotzen et al. |
| 4,707,051 A | | 11/1987 | Hall |
| 4,784,125 A | | 11/1988 | Monticelli et al. |
| 4,890,631 A | | 1/1990 | Hardy |
| 4,985,003 A | | 1/1991 | Francois et al. |
| 5,095,919 A | | 3/1992 | Monticelli et al. |
| 5,181,684 A | * | 1/1993 | Sager ................. 248/231.61 |
| 5,219,349 A | | 6/1993 | Krag et al. |
| 5,320,623 A | * | 6/1994 | Pennig ................. 606/59 |
| 5,330,473 A | * | 7/1994 | Howland ................. 606/250 |
| 5,376,090 A | * | 12/1994 | Pennig ................. 606/54 |
| 5,393,161 A | | 2/1995 | Mata et al. |
| 5,498,098 A | | 3/1996 | Cairns |
| 5,498,264 A | | 3/1996 | Schlapfer et al. |
| 5,501,544 A | | 3/1996 | Cairns |
| 5,624,440 A | | 4/1997 | Huebner |
| 5,662,650 A | | 9/1997 | Bailey et al. |
| 5,709,681 A | * | 1/1998 | Pennig ................. 606/54 |
| 5,741,252 A | | 4/1998 | Mazzio et al. |
| 5,746,741 A | | 5/1998 | Kraus et al. |
| 5,752,860 A | | 5/1998 | Greaves |
| 5,752,954 A | | 5/1998 | Mata et al. |
| 5,769,556 A | * | 6/1998 | Colley ................. 403/24 |
| 5,891,144 A | | 4/1999 | Mata et al. |
| 5,921,985 A | | 7/1999 | Ross, Jr. et al. |
| 5,997,537 A | | 12/1999 | Walulik |
| 6,022,348 A | | 2/2000 | Spitzer |
| 6,080,153 A | * | 6/2000 | Mata et al. ................. 606/54 |
| 6,110,173 A | | 8/2000 | Thomas, Jr. |
| 6,277,119 B1 | | 8/2001 | Walulik et al. |
| 6,342,054 B1 | | 1/2002 | Mata |
| 6,428,540 B1 | | 8/2002 | Claes et al. |
| 6,517,544 B1 | * | 2/2003 | Michelson ................. 606/80 |
| 6,536,982 B2 | * | 3/2003 | Gibbons et al. ................. 403/97 |
| 6,537,279 B1 | * | 3/2003 | Michelson ................. 606/79 |
| 6,575,972 B1 | | 6/2003 | Gordon |
| 6,610,063 B2 | | 8/2003 | Kumar et al. |
| 6,613,049 B2 | * | 9/2003 | Winquist et al. ................. 606/59 |
| 6,616,664 B2 | | 9/2003 | Walulik et al. |
| 6,652,523 B1 | * | 11/2003 | Evrard et al. ................. 606/54 |
| 6,702,814 B2 | * | 3/2004 | Walulik et al. ................. 606/57 |
| 6,730,086 B2 | | 5/2004 | Hehli et al. |
| 6,736,775 B2 | | 5/2004 | Phillips |
| 7,004,943 B2 | | 2/2006 | Ferrante et al. |
| 7,041,103 B2 | * | 5/2006 | Hoffmann-Clair et al. ..... 606/59 |
| 7,048,735 B2 | | 5/2006 | Ferrante et al. |
| 7,241,074 B2 | * | 7/2007 | Thomke et al. ................. 403/385 |
| 7,491,008 B2 | * | 2/2009 | Thomke et al. ................. 403/373 |
| 7,527,626 B2 | * | 5/2009 | Lutz et al. ................. 606/54 |
| 7,789,352 B2 | * | 9/2010 | Darling, III ................. 248/74.4 |
| 2002/0037193 A1 | | 3/2002 | Gibbons et al. |
| 2003/0130662 A1 | * | 7/2003 | Michelson ................. 606/79 |
| 2003/0191467 A1 | * | 10/2003 | Hoffmann-Clair et al. ..... 606/59 |
| 2004/0044344 A1 | | 3/2004 | Winquist et al. |
| 2004/0133200 A1 | | 7/2004 | Ruch et al. |
| 2006/0287652 A1 | * | 12/2006 | Lessig et al. ................. 606/54 |
| 2007/0038217 A1 | * | 2/2007 | Brown et al. ................. 606/57 |
| 2008/0247818 A1 | * | 10/2008 | Oesch et al. ................. 403/389 |

FOREIGN PATENT DOCUMENTS

| | | |
|---|---|---|
| DE | 4103494 | 4/1992 |
| DE | 19753010 | 6/1999 |
| EP | 0 350 925 A1 * | 1/1990 |
| EP | 0350925 | 1/1990 |
| EP | 0490812 | 6/1992 |
| EP | 0524441 | 1/1993 |
| EP | 0604697 | 7/1994 |
| EP | 0838196 | 4/1998 |
| EP | 1184000 | 3/2002 |
| FR | 2693648 | 1/1994 |
| GB | 2033758 | 5/1980 |
| JP | 08-071084 | 3/1996 |
| JP | 2002-515782 | 5/2002 |
| JP | 2002-533153 | 10/2002 |
| KR | 10-0166622 | 4/1996 |
| WO | WO 88/01152 * | 2/1988 |
| WO | WO 88/01152 A1 * | 2/1988 |
| WO | WO 9532676 | 12/1995 |
| WO | 2004/112625 | 12/2004 |

\* cited by examiner

ADJUSTABLE FIXATION CLAMP AND METHOD

FIELD OF THE INVENTION

The present invention relates to a fixation clamp and, more particularly, to an adjustable fixation clamp for use in an external fixation system for holding bone fragments adjacent to each other.

BACKGROUND OF THE INVENTION

External fixation systems are used to connect two or more bone fragments to each other. For example, external fixation systems have been used to reduce fractures of the mandible, including fractures of the condyle. These devices incorporate bone screws, pins, wires, rods, bars and/or rings to assist in healing of fractured bones and to assure proper alignment of bone.

To provide for external fixation of a bone fracture, at least four points of fixation are generally preferred. Two bone screws, pins or wires are inserted into each bone fragment on opposite sides of a fracture. The bone screws, pins or wires are connected to a fixation rod, bar or ring using clamps, thereby creating an external fixation system. Such a configuration prevents bone fragments from rotating and/or translating relative to each other.

Clamps which allow for a screw, pin or wire to be clipped in from the side are particularly useful in bone fixation. These clamps, however, are configured to attach a single screw, pin or wire to a rod, bar or ring. With current clamps, this requires the use of at least four separate clamps in an external fixation system with four points of fixation, thereby resulting in a bulky fixation system. Thus, it is desirable to have a clamp which can connect multiple screws, pins or wires to a fixation rod, bar or ring thereby reducing the size of a fixation system.

SUMMARY OF THE INVENTION

The present invention relates to an adjustable fixation clamp having a longitudinal axis, a first clamp assembly, a second clamp assembly, and a shaft which may join the first and second clamp assembly and may be positioned therethrough preferably along the longitudinal axis. The shaft may have a head portion and a threaded portion which may receive a connection device, such as a nut. In another embodiment, at least one clamp assembly may have internal threads for engaging the threaded portion of the shaft. The first and second clamp assemblies may be rotatable relative to each other about the longitudinal axis and may be selectively fixed relative to each other.

The first clamp assembly may have a first and second vise plate. The first vise plate may have a bore and at least two spaced apart recesses, which may be parallel to each other and the second vise plate may have a bore and at least two corresponding spaced apart recesses, which may be parallel to each other. The recesses of the first and second vise plate may define at least first and second receiving portions. The first and second vise plates may also define first and second insertion portions, which may be at an angle to and which may communicate with the first and second receiving portions. Moreover, the second clamp assembly may have a third and fourth vise plate. The third vise plate may have a bore and at least two spaced apart and generally parallel recesses. The fourth vise plate may have a bore and at least two corresponding spaced apart and generally parallel recesses such that the third and fourth vise plates may define at least third and fourth receiving portions. The third and fourth vise plates may also define third and fourth insertion portions, which may be at an angle to and which may communicate with the third and fourth receiving portions. At least a pair of fixation components (e.g., screw, pin or wire) may be inserted through the insertion portions and into the receiving portions of one clamp assembly and at least one connector (e.g., rod, bar and/or ring) may be inserted through the insertion portions and into the other clamp assembly. The fixation components and/or connector(s) may be inserted through the insertion portions and into the receiving portions in a direction which may be perpendicular or oblique to the longitudinal axis.

The shaft may be positioned through the bores in the vise plates, which may collectively form a longitudinal bore. In such a construction, the first receiving portion may be positioned on a first side of the longitudinal bore and the second receiving portion may be positioned on a second, opposite side of the longitudinal bore. Furthermore, the third receiving portion may be positioned on the first side of the longitudinal bore and the fourth receiving portion may be positioned on the second, opposite side of the longitudinal bore. The bores and, consequently, the longitudinal bore may extend in a direction which may be at an angle with respect to the receiving portions.

The vise plates may be configured so as to prevent rotation about the longitudinal axis between the first and second vise plates as well as between the third and fourth vise plates. In one embodiment, the first vise plate may have at least one post which may be positioned within at least one opening of the second vise plate. In another embodiment, the second vise plate may have at least one post which may be positioned within at least one opening of the first vise plate. In another embodiment, the third vise plate may have at least one post which may be positioned within at least one opening of the fourth vise plate. In yet another embodiment, the fourth vise plate may have at least one post which may be positioned within at least one opening of the third vise plate. Such constructions may allow the first and second vise plates and/or third and fourth vise plates to move axially along the longitudinal axis with respect to each other and/or to be angled with respect to each other.

Furthermore, the clamp assemblies may be configured to prevent rotation with respect to each other. In one embodiment, each clamp assembly may have a serrated portion. A biasing member such as a spring may be positioned between the first and second clamp assemblies to separate the first and second clamping assemblies and serrated portions from each other. In this way, the clamping assemblies may be rotated 360° about the longitudinal axis with respect to each other prior to fixing the orientation of the clamp assemblies. Upon tightening the nut or screwing the threaded portion of the shaft into internal threads of the clamp assemblies, the serrated portions may engage each other and the clamp assemblies may be fixed with respect to each other.

In use, the adjustable fixation clamp may be used to connect at least two fixation components (e.g., screw, pin or wire) to one or more connectors( e.g., rod, bar and/or ring). A first end of at least two fixation components may be inserted into a bone fragment. The other end of the fixation components may be inserted (e.g., clipped or snapped) into receiving portions of one of the clamp assemblies (e.g., the first and second receiving portions of the first clamp assembly) of a first adjustable clamp. At least a second set of fixation components may be inserted into an adjacent bone fragment and may be inserted into receiving portions of one of the clamp assemblies (e.g., the first and second receiving portion of the first clamp assembly) of a second adjustable clamp. At least one connector may be positioned between the first and second adjustable clamps and may be received in the receiving portions of one of the clamp assemblies of each adjustable clamp (e.g., third and/or fourth receiving portion of the first and second adjustable clamp). In this way, an exemplary external fixation system may be formed. Once the screws, pins, wires, rod(s), bar(s) and/or ring(s) are adjusted to a desired orientation, the nuts of the clamps may be tightened to fix the position of the screws, pins, wires, rod(s), bar(s) and/or ring(s). In another embodiment, the threaded portion of the shaft may be screwed into internal threads of the clamp assembly. In some embodiments, more than two adjustable clamps may be used to create an external fixation system One method may comprise providing a clamp, inserting (e.g., clipping or snapping) the at least two fixation components into a first bone segment, positioning the a fixation element into each of the first and second receiving portions of the clamp through the first and second insertion portions, positioning at least one connector into at least one of the third and fourth receiving portions of the clamp (e.g., through the third and fourth insertion portions), and locking the first and second assemblies with respect to each other. The step of inserting the at least two fixation components into a first bone segment may further comprise inserting at least one of the fixation components through a guide. In addition, the method may comprise providing a second clamp, inserting at least two additional fixation components into a second bone segment, attaching the second clamp to the at least two additional fixation components and the connector, and locking the at least two additional fixation components with respect to the connector. In another method, a pair of sloping surfaces may be positioned proximate at least one of the first, second, third and fourth receiving portions and the positioning step may further comprise inserting at least one fixation element between a pair of sloping surfaces. In yet another method, the positioning step may further comprise inserting at least one connector between a pair of sloping surfaces.

BRIEF DESCRIPTION OF THE DRAWINGS

The present invention can be better understood by reference to the following drawings, wherein like references numerals represent like elements. The drawings are merely exemplary to illustrate certain features that may be used singularly or in combination with other features and the present invention should not be limited to the embodiments shown.

DETAILED DESCRIPTION

Figure 1:
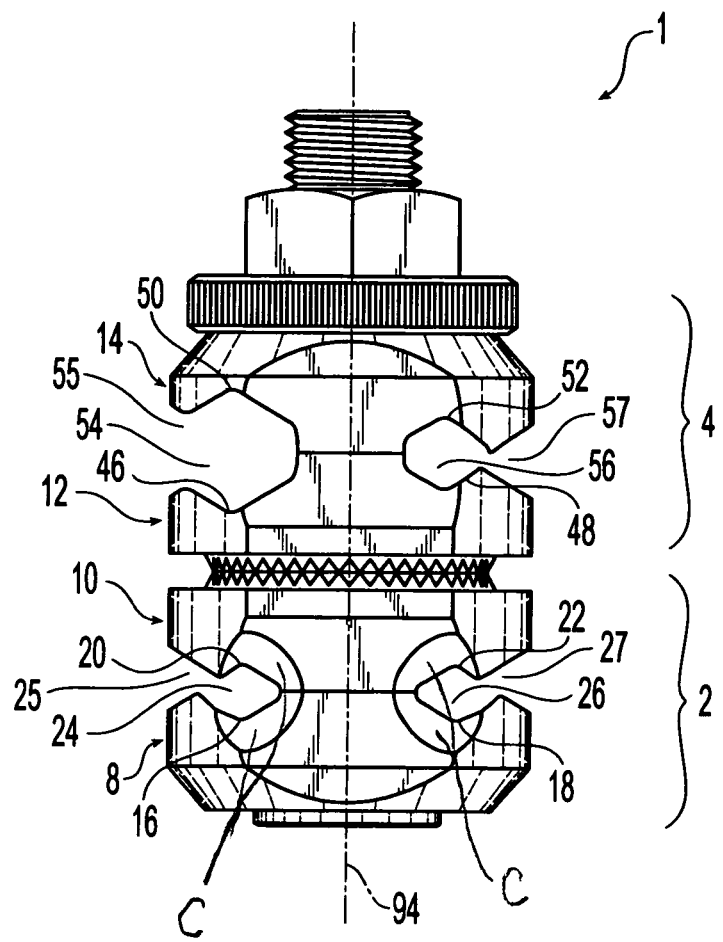
FIG. 1 is a front view of an exemplary embodiment of the clamp of the present invention.
Figure 2:
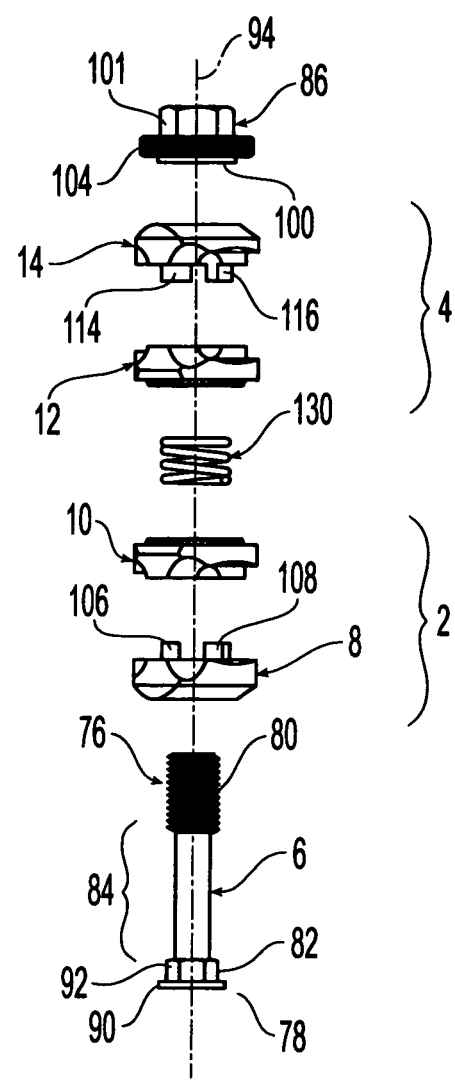
FIG. 2 is an exploded view of the clamp of FIG. 1.

As shown in FIGS. 1 and 2, the adjustable clamp 1 may include a first clamp assembly 2 and a second clamp assembly 4. The clamp assemblies 2, 4 may be connected to each other by a shaft 6, which may be positioned through a longitudinal bore in the clamp assemblies 2, 4. The shaft 6 may be positioned along the longitudinal axis 94 of the adjustable clamp 1. It should, however, be understood that those of ordinary skill in the art will recognize many modifications and substitutions which may be made to various elements of the present invention.

The first clamp assembly 2 may have a lower or first vise plate 8 and an upper or second vise plate 10. Similarly, the second clamping portion 4 may include a lower or third vise plate 12 and an upper or fourth vise plate 14. Vise plates 8, 10, 12 and 14 may be made of any suitable material, preferably biocompatable material, such as metal (e.g., stainless steel, titanium, aluminum), plastic, rubber, an alloy of two or more materials (e.g., titanium-aluminum-vanadium) or a composite material (i.e., made up of two or more materials). Those skilled in the art will appreciate that any component of the clamp 1 may be made of these materials. Moreover, those skilled in the art will appreciate that different components of the clamp 1 may be made of different materials—for example, in one embodiment, the shaft 6 and/or the nut 86 may be made of stainless steel, the biasing member 130 may be made of elgiloy and the vise plates 8, 10, 12 and/or 14 may be made of titanium.

The first clamp assembly 2 may be sized and configured to receive at least two fixation components such as a screw, pin and/or wire. In an alternative embodiment, the first clamp assembly 2 may receive at least one connector such as a rod, bar and/or ring. The second clamp assembly 4 may be sized and configured to receive at least one elongated connector such as a rod, bar or ring. In another embodiment, the second clamp assembly 4 may be sized and configured to receive at least two fixation components such as a screw, pin and/or wire.

Figure 3A:
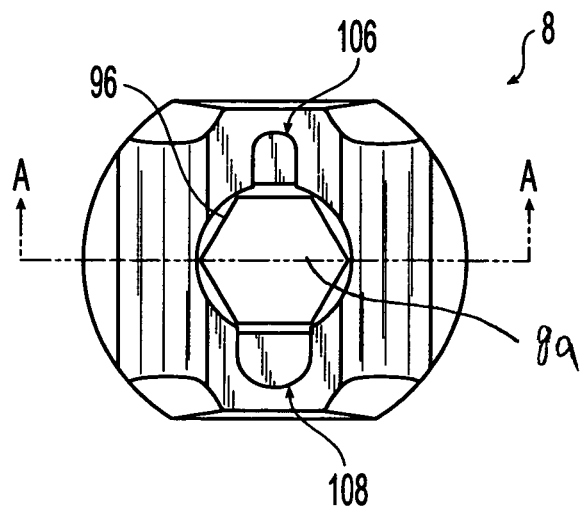
FIG. 3A is a top view of an exemplary embodiment of a first vise plate of the present invention.
Figure 3B:
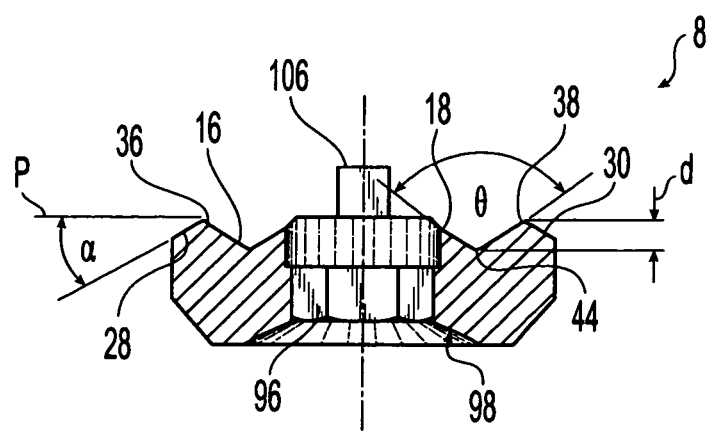
FIG. 3B is a cross-sectional view of the first vise plate of FIG. 3A along line A-A.
Figure 4A:
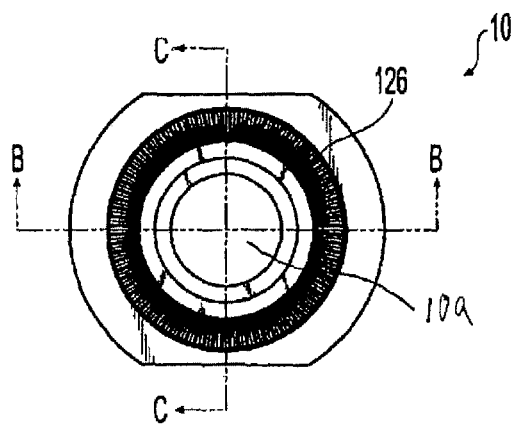
FIG. 4A is a top view of an exemplary embodiment of a second vise plate of the present invention.
Figure 4B:
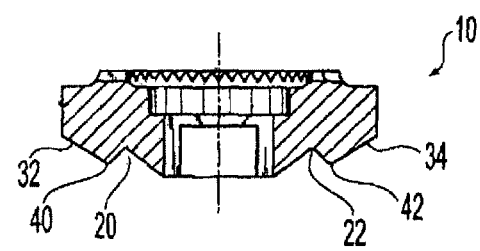
FIG. 4B is a cross-sectional view of the second vise plate of FIG. 4A along line B-B.

As illustrated in FIG. 3B, the first vise plate 8 of the first clamp assembly 2 may include two recesses 16 and 18, and a bore 8*a*. As shown in FIG. 4B, the second vise plate 10 may have a bore 10*a*, and recesses 20 and 22. The recesses 20 and 22 may correspond to recesses 16 and 18, respectively, to define a first receiving portion 24 and a second receiving portion 26, respectively (FIG. 1). In some embodiments, the first and second vise plate 8, 10 may have more than two recesses and, consequently, may have more than two receiving portions. The first and second vise plates 8, 10 may also define a first insertion portion 25 and a second insertion portion 27, which may be at an angle (e.g., perpendicular or oblique) with respect to the receiving portions 24, 26 and which may communicate with the receiving portions 24, 26. The receiving portions 24, 26 may be the same size or different sizes such that the receiving portions 24, 26 may receive the same or different sized fixation components and/or connectors.

The recesses 16 and 18, 20 and 22 may be oriented parallel to each other or may be at an angle relative to each other.

Consequently, the receiving portions 24 and 26 may be parallel to each other or at an angle relative to each other. In a preferred embodiment, a set of wires (e.g., a Kirschner wire) may be captured within the first and second receiving portion 24, 26. It will be appreciated, however, that a set of any fixation components such as, for example, a set of screws, a set of pins may be held within the receiving portions 24 or 26. Alternatively, the receiving portions 24, 26 may receive at least one connector such as, for example, a rod, bar or ring.

To accommodate at least two fixation components, the recesses 16, 18, 20 and 22 and, consequently, receiving portions 24, 26 may have the same dimension. For example, the receiving portions 24, 26 may be sized to each receive a wire having a diameter of between about 0.8 mm and about 8.0 mm, more preferably, between about 1.0 mm and about 6.0 mm and, most preferably, between about 2.0 mm and about 2.5 mm. Moreover, as shown in FIGS. 1, 3B and 4B, the recesses 16, 18, 20, 22 may be generally V-shaped in cross section. The V-shape may have an angle θ, for example, between about 45 degrees and 160 degrees, more preferably between about 100 degrees and about 135 degrees and, most preferably, between about 110 degrees and 130 degrees. It should be noted that the angles θ for recesses 16 and 18, recesses 20 and 22, recesses 16 and 20, recesses 18 and 22 may be the same or different. It will be appreciated by those skilled in the art that the cross section of the recesses 16, 18, 20 and 22 may be any other shape (e.g., half-rounded, U-shaped, polygonal) and may have a dimension of, for example, between about 0.5 mm and about 8.5 mm, more preferably, between about 1.0 mm and about 6.0 mm and, most preferably, between about 2.0 mm and about 3.0 mm.

To assist in inserting (e.g., clipping or snapping) a screw, pin, wire, rod, bar or ring into receiving portions 24 and 26, the first vise plate 8 may have sloping surfaces 28 and 30 and the second vise plate 10 may have sloping surfaces 32 and 34. The insertion portion 25 may be located between the sloping surfaces 28 and 32 such that the sloping surfaces 28, 32 may define the insertion portion 25, and the insertion portion 27 may be located between sloping surfaces 30 and 34 such that the sloping surfaces 30, 34 may define the insertion portion 27. The sloping surfaces 28, 30, 32 and 34 may slope at an angle a relative to a horizontal plane P (i.e., a plane which may be perpendicular to the longitudinal axis 94). For example, as shown in FIG. 3B, the sloping surfaces 28 may slope at an angle α between about 5 degrees and about 80 degrees, more preferably, between about 10 degrees and about 50 degrees and, most preferably, between about 20 degrees and 40 degrees. The sloping surfaces 28 and 32, 30 and 34 may help guide a screw, pin, wire, rod, bar or ring into the receiving portions 24 and 26, respectively. It should be noted that the angles a for sloping surfaces 28 and 30, sloping surfaces 32 and 34, sloping surfaces 28 and 32, sloping surfaces 30 and 34 may be the same or different.

The receiving portions 24 and 26 may hold at least two fixation components, for example, a set of wires such that the longitudinal axis of the fixation components may be parallel with each other. Moreover, the receiving portions 24 and 26 may be spaced from each other such that the longitudinal axis of the fixation components may be between about 5 mm and about 25 mm apart, more preferably, between about 6 mm and about 15 mm apart and, most preferably between about 6 mm and about 8 mm apart.

In addition, the first vise plate 8 may have lip portions 36 and 38 and the second vise plate 10 may have lip portions 40 and 42. The lip portion 36 may be formed at the boundary where the recess 16 meets the sloped surface 28 and the lip portion 38 may be formed at the boundary where the recess 18 meets the sloped surface 30. Moreover, the lip portion 40 may be formed at the boundary where the recess 20 meets the sloped surface 32, and the lip portion 42 may be formed at the boundary where the recess 22 meets the sloped surface 34. The lip portions 36, 38, 40 and 42 may extend a distance above the vertex of each recess. For example, as shown in FIG. 3B, the lip portion 38 may extend a distance d above the vertex 44 of the recess 18 of between about 0.5 mm and about 5.0 mm, more preferably, between about 0.7 mm and about 3.0 mm and, most preferably, between about 0.8 mm and about 1.0 mm. The lip portions 36, 40 and 38, 42 may prevent a screw, pin, wire, rod, bar or ring from slipping out of the receiving portions 24 and 26, respectively. It should be noted that while a lip may be formed by the intersecting of a recess and a sloping surface, a lip may be formed in numerous other ways and may be any structure which may prevent a screw, pin, wire, rod, bar or ring from slipping out the receiving portions 24 and 26.

Furthermore, while FIGS. 1, 3B and 4B illustrate an embodiment where each vise plate 8 and 10 may have two sloping surfaces and two lips, the vise plates 8 and 10 may be configured to have any combination of sloping surfaces and lips. For instance, proximate the receiving portion 24, vise plate 8 may not have a sloping surface (e.g., α=0°) and vise plate 10 may have a sloping surface 32 and/or vise plate 8 may have a lip portion 36 and vise plate 10 may not have a lip portion.

Figure 5A:
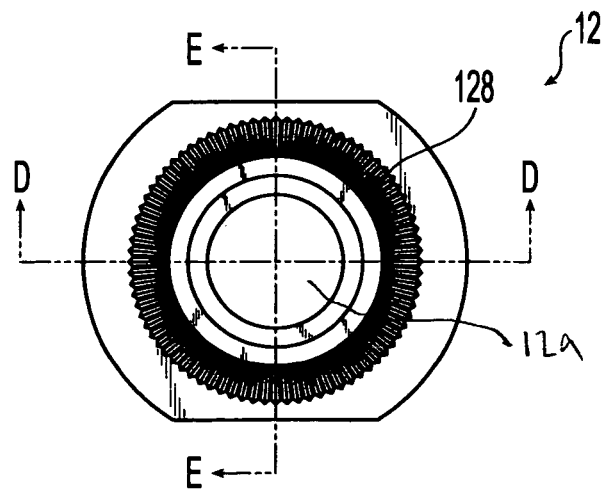
FIG. 5A is a bottom view of an exemplary embodiment of a third vise plate of the present invention.
Figure 5B:
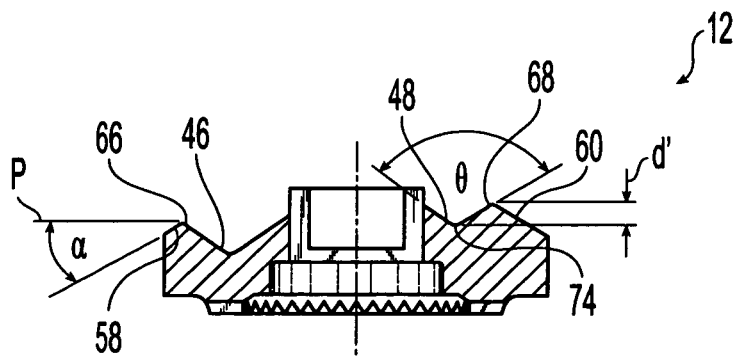
FIG. 5B is a cross-sectional view of the third vise plate of FIG. 5A along line D-D.
Figure 6A:
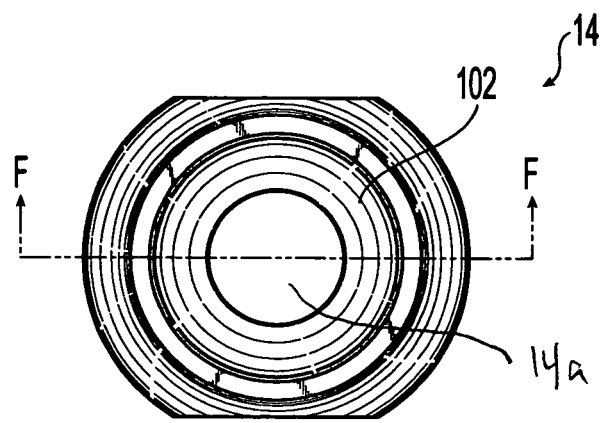
FIG. 6A is a top view of an exemplary embodiment of a fourth vise plate of the present invention.
Figure 6B:
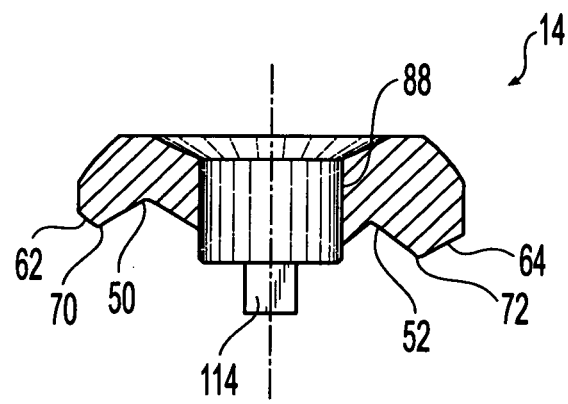
FIG. 6B is a cross-sectional view of the fourth vise plate of FIG. 6A along line F-F.

Referring now to FIG. 5B, the third vise plate 12 of the second clamp assembly 4 may include two parallel recesses 46 and 48, and a bore 12a. As shown in FIG. 6B, the fourth vise plate 14 may have a bore 14a, and recesses 50 and 52. The recesses 50, 52 may correspond to recesses 46 and 48, respectively, to define a first receiving portion 54 and a second receiving portion 56, respectively (FIG. 1). In a preferred embodiment, at least one rod may be captured within the third and/or fourth receiving portion 54, 56. It will be appreciated, however, that any fixation component such as, for example, a screw, pin, wire or connector, such as, for example, a bar or ring may be held within the receiving portions 54 and/or 56. In some embodiments, the third and fourth vise plate 12, 14 may have more than two recesses and, consequently, may have more than two receiving portions. The third and fourth vise plates 12, 14 may also define a third insertion portion 55 and a fourth insertion portion 57, which may be at an angle (e.g., perpendicular or oblique) with respect to the receiving portions 54, 56 and which may communicate with the receiving portions 54, 56.

To accommodate different fixation components and/or connectors, the recesses 46, 48, 50 and 52 and, consequently, receiving portions 54, 56 may be different sizes. For example, the receiving portions 54, 56 may be sized to receive a rod with a diameter of between about 0.8 mm and about 12 mm, more preferably, between about 2.0 mm and about 6.0 mm and, most preferably, between about 2.5 mm and about 4.0 mm. Moreover, as shown in FIGS. 1, 5B and 6B, the recesses 46, 48, 50 and 52 may be generally V-shaped in cross section. Similar to the first and second vise plates 8, 10, the V-shape of the third and fourth vise plates 12, 14 may have an angle θ, for example, between about 45 degrees and 160 degrees, more preferably between about 100 degrees and about 135 degrees and, most preferably, between about 110 degrees and 130 degrees. It should be noted that the angles θ for recesses 46 and 48, recesses 50 and 52, recesses 46 and 50, recesses 48 and 52 may be the same or different. It will be appreciated by those skilled in the art that the cross section of the recesses 46, 48, 50 and 52 may be any other shape (e.g., rounded, U-shaped, polygonal).

To assist in inserting (e.g., clipping or snapping) a screw, pin, wire, rod, bar or ring into receiving portions 54 and/or 56, the third vise plate 12 may have sloping surfaces 58 and 60 and the fourth vise plate 14 may have sloping surfaces 62 and 64. The insertion portion 55 may be located between the sloping surfaces 58 and 62 such that the sloping surfaces 58, 62 may define insertion portion 55, and the insertion portion 57 may be located between sloping surfaces 60 and 64 such that the sloping surfaces 60, 64 may define the insertion portion 57. Similar to the first and second vise plate 8, 10, the sloping surfaces 58, 60, 62 and 64 may slope at an angle relative to a horizontal plane P (i.e., a plane which may be perpendicular to the longitudinal axis 94). For example, as shown in FIG. 5B, the sloping surfaces 58 may slope at an angle a between about 5 degrees and about 80 degrees, more preferably, between about 10 degrees and about 50 degrees and, most preferably, between about 20 degrees and 40 degrees. The sloping surfaces 58 and 62, 60 and 64 may help guide a screw, pin, wire, rod, bar or ring into the receiving portions 54 and 56, respectively. It should be noted that the angles a for sloping surfaces 58 and 60, sloping surfaces 62 and 64, sloping surfaces 58 and 62, sloping surfaces 60 and 64 may be the same or different.

In addition, as shown in FIGS. 5B and 6B, the third vise plate 12 may have lip portions 66 and 68 and the fourth vise plate 14 may have lip portions 70 and 72. The lip portion 66 may be formed at the boundary where the recess 46 meets the sloped surface 58 and the lip portion 68 may be formed at the boundary where the recess 48 meets the sloped surface 60. Moreover, the lip portion 70 may be formed at the boundary where the recess 50 meets the sloped surface 62, and the lip portion 72 may be formed at the boundary where the recess 52 meets the sloped surface 64. The lip portions 66, 68, 70 and 72 may extend a distance above the vertex of each recess. For example, as shown in FIG. 5A, the lip portion 68 may extend a distance d' above the vertex 74 of the recess 48 of between about 0.5 mm and about 5.0 mm, more preferably, between about 0.7 mm and about 3.0 mm and, most preferably, about 0.8 mm and about 1.0 mm. The lip portions 66 and 70, and 68 and 72 may prevent a screw, pin, wire, rod, bar or ring from slipping out of the receiving portions 54 and 56, respectively. It should be noted that while a lip may be formed by the intersecting of a recess and a sloping surface, a lip may be formed in numerous other ways and may be any structure which may prevent a screw, pin, wire, rod, bar or ring from slipping out the receiving portions 54 and 56.

Furthermore, while FIGS. 1, 5B and 6B illustrate an embodiment where both vise plates 12 and 14 may have two sloping surfaces and two lips, the vise plates 12 and 14 may be configured to have any combination of sloping surfaces and lips. For instance, proximate the receiving portion 54, vise plate 12 may not have a sloping surface (e.g., α=0°) and vise plate 14 may have a sloping surface 62 and/or vise plate 12 may have a lip portion 66 and vise plate 14 may not have a lip portion.

Referring again to FIG. 2, the first and second clamp assemblies 2, 4 may be connecting to each other by positioning the shaft 6 through the bores 8a, 10a, 12a and 14a, which may collectively form a longitudinal bore. In such a construction, the receiving portion 24 may be positioned on a first side of the longitudinal bore and the receiving portion 26 may be positioned on a second, opposite side of the longitudinal bore. Furthermore, the receiving portion 54 may be positioned on the first side of the longitudinal bore and the receiving portion 56 may be positioned on the second, opposite side of the longitudinal bore. The bores 8a, 10a, 12a and 14a and, consequently, the longitudinal bore may extend in a direction which may be at an angle (e.g., perpendicular) with respect to the receiving portions 24, 26, 54, 56.

The shaft 6 may have a distal end 76 and a proximal end 78. The distal end 76 may have a threaded portion 80 and the proximal end may have a head portion 82. The threaded portion may be positioned on an external surface of the shaft 6. However, in another embodiment, the threaded portion may be within a cavity (not shown) in the distal end 76 of the shaft 6 such that a fastener such as, for example, a bolt may be threaded into the cavity and engage the internal threads. As shown in FIG. 2 the distal end 76 may be larger than a reduced diameter portion 84 of the shaft 6, which is located between the distal end 76 and the head portion 82. Such a construction may prevent the thickness of the shaft 6 from interfering with rotation of the clamp assemblies 2, 4 relative to each other.

The threaded portion 80 may engage a connection device, for example, a nut 86 such that rotation of the nut 86 in a first direction causes the nut 86 to move toward the head portion 82 (i.e., tightening the nut). Upon tightening the nut 86, the clamp assemblies 2, 4 and vise plates 8, 10, 12 and 14 may be rotationally and translationally fixed with respect to each other and held between the nut 86 and the head portion 82. It should be noted that tightening the nut 86 may lock two or more fixation components (e.g., screw, pin or wire) and one or more connectors (e.g., rod, bar and/or ring) simultaneously with the clamp 1. The nut 86 may be rotated in a second direction such that the nut 86 may move away from the head portion 82 (i.e., loosening the nut). As the nut is loosened, the clamp assemblies 2, 4 and vise plates 8, 10, 12 and 14 may be free to move with respect to each other such that a screw, pin, wire, rod, bar and/or ring may be inserted in or removed from the receiving portion 24, 26, 54 and 56. To prevent the nut 86 from separating from the shaft 6 upon loosening of the nut 86, the threaded portion 80 may be deformed at its distal most end. In another embodiment (not shown), the threaded portion 80 may be threaded into internal threads (not shown) on inner wall 88 (FIG. 6B) of the fourth vise plate 14 and a nut 86 may be unnecessary. It will be appreciated that any means of fixing the first and second clamp assemblies 2 and 4 with respect to each other is envisioned.

In one embodiment, the head portion 82 may have a flange 90 and an engaging portion 92. The engaging portion 92 may be any shape, including elliptical, square, rectangular, hexagonal or some other polygon. The engaging portion 92 may be positioned in an opening 96 (FIG. 3B) in the first vise plate 8 which may have a corresponding shape to the engaging portion 92. The engagement between same-shaped portion 92 and opening 96 may cause the shaft to be rotationally fixed with respect to the first clamp assembly 2. It should be noted that the engaging portion 92 and opening 96 may be configured in any way so long as the engaging portion 92 and opening 96 may mate to prevent the rotation of the shaft 6. For example, the engaging portion 92 may be round and may comprises a protrusion (not shown) which may engage a corresponding protrusion of the opening 96. The rotation of the shaft 6 may be prevented when the two protrusions contact each other. Moreover, the head portion 82 may have a flange 90, which may be positioned in receiving opening 98. The flange 90 may help move the clamp assemblies 2, 4 and vise plates 8, 10, 12 and 14 towards the nut 86 as the nut 86 is tightened. The nut 86 may be threaded towards and away from the head portion 82 while the shaft 6 may be prevented from rotational and translational movement within the clamp assemblies 2, 4. Those skilled in the art will appreciated that, in another embodiment (not shown), the head portion 82 of the shaft 6 may be positioned proximate the fourth vise plate 14 and the connection device (e.g., nut 86) may be positioned proximate the first vise plate 8. In such an embodiment, the first vise plate 8 may be configured to be similar or identical to the fourth vise plate 14 and the fourth vise plate 14 may be configured to be similar or identical to the first vise plate 8.

In an alternative embodiment, the head portion 82 of the shaft 6 may be configured so that it may rotate within the vise plate 8. A protrusion 100 of the nut 86 may engage a recess 102 (FIG. 6A) such that the nut 86 may be prevented from rotating with respect to the fourth vise plate 14. For example, the protrusion 100 may have a hexagonal shape and the recess 102 may have a corresponding hexagonal shape.

The nut 86 may comprise a shaped head portion 101 and a gripping surface 104. The head portion 101 and gripping surface 104 may be any shape so long as an operator may grasp the nut 86 with a tool and/or his/her fingers and rotate the nut 86. The gripping surface may be roughened, textured, serrated, knurled or the like to facilitate gripping the nut 86 to tightened or loosen the nut 86.

Figure 4C:
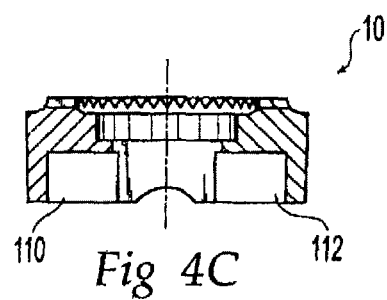
FIG. 4C is a cross-sectional view of the second vise plate of FIG. 4A along line C-C.
Figure 5C:
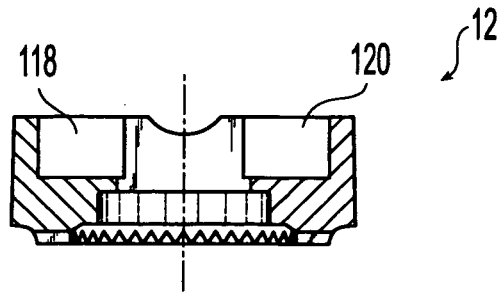
FIG. 5C is a cross-sectional view of the third vise plate of FIG. 5A along line E-E.

The vise plates 8, 10, 12 and 14 may incorporate a feature which may prevent the vise plates 8, 10, 12 and/or 14 from rotating with respect to each other about the longitudinal axis 94 and may keep recesses 16, 18, 46, 48 aligned with 20, 22, 50, 52, respectively. For example, as shown in FIGS. 3A and 3B, the first vise plate 8 may have two posts 106 and 108, which may be inserted in post receiving openings 110 and 112, respectively (FIG. 4C). Similarly, as shown in FIG. 2, the fourth plate 14 may have two posts 114 and 116 which may engage post receiving openings 118 and 120, respectively (FIG. 5C). The post receiving openings 110, 112, 118, and 120 may be any shape and sized such that posts 106, 108, 114 and 116, respectively, may move therein upon insertion of the screw, pin, wire, rod, bar or ring into receiving portions 24, 26, 54 and/or 56. In particular, the post 106 and 108 may rotate within post receiving openings 110 and 112 and/or translation along the longitudinal axis 94. It should be noted that a vise plate may have a single post, which may be received in a single receiving opening of another vise plate. Moreover, those skilled in the art will appreciate that any structure which prevents rotation of vise plate 8 with respect to vise plate 10 and vise plate 12 with respect to vise plate 14 is envisioned.

Furthermore, the clamp assemblies 2 and 4 may be configured such that the assemblies 2 and 4 may be prevented from rotating with respect to each other. As illustrated in FIGS. 4A and 5A, the second and third vise plate 10 and 12 may have serrated portions 126 and 128, respectively. Such a construction may enable the second and third vise plates 10 and 12 to be selectively fixed with respect to each other. It should be noted that the serrated portion 126 and 128 may be integral with the second and third vise plates 10 and 12, respectively, or may be part of a separate structure from the vise plates—for example, the serrated portions 126 and 128 may be part of two separate washers (not shown) which may be positioned adjacent to each other and in between vise plates 10 and 12, respectively. Such a construction may also fix the first and second clamp assemblies 2, 4 with respect to each other.

Upon loosening the nut 86, the serrated portions 126 and 128 may be separated and, thereby, may allow the second and third vises plates 10, 12 and/or the first and second clamp assemblies 2, 4 to rotate about the longitudinal axis 94 with respect to each other—the clamp assemblies 2 and 4 may rotate 360° relative to each other about the longitudinal axis 94. Upon tightening the nut 86, serrated portions 126 and 128 may be brought together such that second and third vises plates 10, 12 and/or the first and second clamp portions 2, 4 may be fixed against rotation.

In order to facilitate rotation of the second and third vises plates 10, 12 and/or the first and second clamp portions 2, 4, a biasing member 130 may be positioned between the serrated portion 126 and 128 to keep the serrated portions 126 and 128 from engaging each other. The biasing member 130 may be, for example, a coil spring, a wave spring, a bellows spring, a rubber element, a flexible plastic element or the like. The biasing member 130 may also bias the first vise plate 8 towards the second vise plate 10 and/or may bias the third vise plate 12 towards the fourth vise plate 14. In this way, a screw, pin, wire, rod, bar and/or ring may be clipped and/or snap-fit into receiving portions 24, 26, 54 and/or 56 by pushing the screw, pin, wire, rod, bar and/or ring into receiving portions 24, 26, 54 and/or 56 in a direction perpendicular or oblique to the longitudinal axis 94. It will be appreciated by those skilled in the art, however, that a biasing member 130 may be positioned between the first and second vises plates 8, 10, between the third and fourth vise plates 12, 14, between the first vise plate 8 and the head portion 82, and/or between the fourth vise plate 14 and the nut 86.

Figure 7:
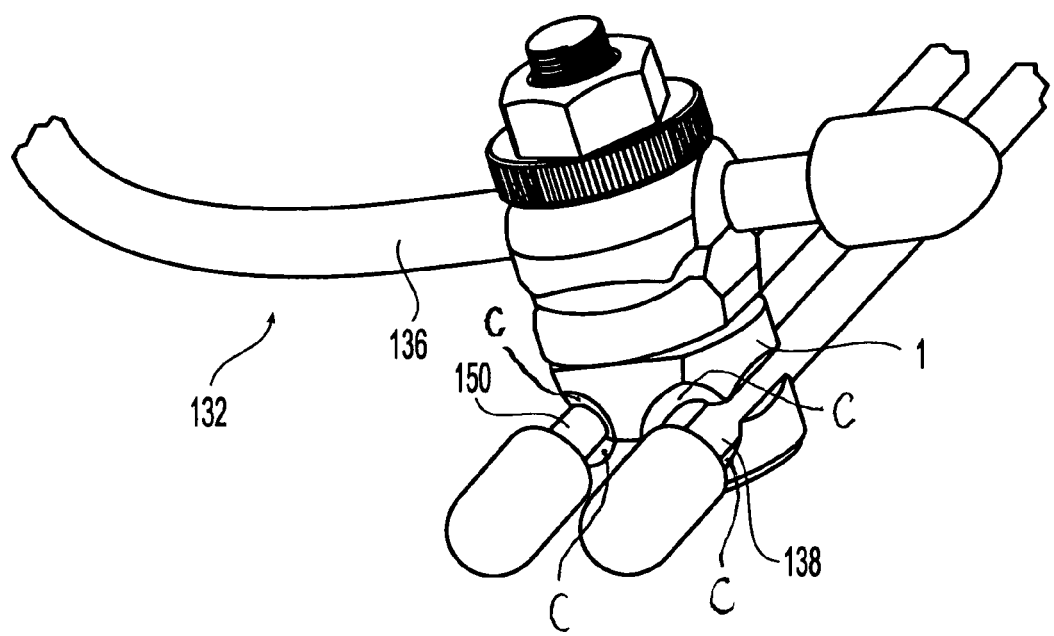
FIG. 7 is a perspective view an exemplary embodiment of a portion of an external fixation system incorporating the clamp of FIG. 1.

FIG. 7 illustrates the adjustable clamp 1 being used as part of an external fixation device 132. It should be noted, however, that the adjustable clamp 1 may be incorporated into an external fixation system for use with any bone, for example, mandible (condyle), hand, distal radius (wrist), ankle, feet, vertebrae, rib and long bones. Moreover, while FIG. 7 shows a single clamp 1 of an external fixation system 132, a fixation system may incorporate a number of clamps 1.

Figure 8:
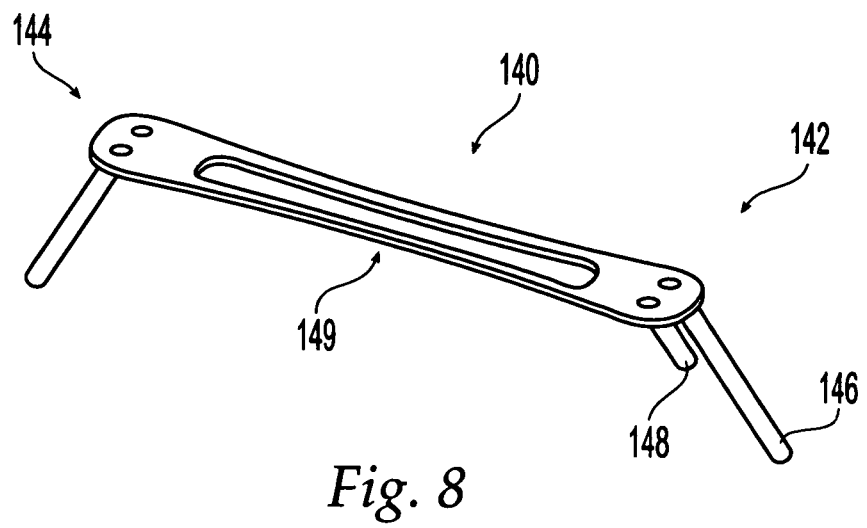
FIG. 8 is a perspective view of an exemplary embodiment of an inserter.

The adjustable clamp 1 may connect the fixation rod 136 with two or more wires (e.g., a Kirschener wire). In order to connect a wire 138, 150 to the fixation rod 136, the wire 138, 150 may first be inserted into the bone (e.g., mandible) using a guide 140 (FIG. 8). It should be understood by those skilled in the art that a guide, which may be any type of hollow structure (e.g., a tube or cannula), may be used to insert a screw, pin or wire into bone.

The guide 140 may have a first side 142 for inserting, for example, 2.0 mm Kirschener wires and a second side 144 for inserting, for example, 2.5 mm Kirschener wires. Each side 142, 144 may also have a first tissue protector 146 and a second, shorter tissue protector 148. In a procedure using wires, a surgeon may create a stab incision in the skin and may insert an obturator (not shown) and first tissue protector 146 through tissue until the obturator contacts bone. The obturator may be removed and the tissue protection 146 may be held against bone. A surgeon may use the handle 149 to guide the tissue protector 146 towards bone. Once the first tissue protector 146 is in position, a surgeon may insert the wire 138 into bone. The wire 138 may have a self-drilling tip such that rotation of the wire 138 may result in the wire 138 being drilled into bone. After the wire 138 is fixed in bone, the first tissue protector 146 may be removed from the body.

Thereafter, a second wire 150 may be inserted into bone next to the wire 138. In such a procedure, after the wire 138 is fixed in bone and the first tissue protector 138 is removed from the body, the surgeon may create a second stab incision through the skin. It will be appreciated however, that the first incision may be made large enough for inserting both wire 138 and a second wire 150. To insert a second wire 150, an obturator (not shown) and the first tissue protector 146 may be inserted through tissue until the obturator contacts bone. Further, the guide 140 may be oriented such that the wire 138 slides through the second tissue protector 148 as the first tissue protector 146 is inserted into the body. Such a construction keeping the wire 138 and the second wire 150 a fixed distance apart so that the wire 138 and the second wire 150 may eventually be fit into the receiving portions 24 and 26 of clamp assembly 2. The second wire 150 may then be drilled into bone, and the tissue protector 146 and the second tissue protector 148 (i.e., assuming the second tissue protector 148 is in the body) may be removed from the body. Finally, the first and second wires 138, 150 may be clipped into the clamp assembly 2 of a first clamp 1. The step of inserting the wires 138, 150 may be repeated on the other side of a bone fracture using a second clamp 1 (not shown). Those skilled in the art will appreciate that more than two clamps 1 may be used to form an external fixation system (e.g., where there are multiple fracture of a bone or where multiple fixation components are to be inserted into each side of a bone fracture). Further, it should be noted that fixation components such as screws or pins may be used in place of wires 138, 150. A connector, such as a rod, bar or ring may then be positioned between the two clamps 1 and may be clipped into the second clamp assemblies 4 of the first and second clamps 1.

In use, the adjustable clamp 1 may be clipped or snapped onto a screw, pin, wire, rod, bar and/or ring when the nut 86 is in a loosed condition. This may be accomplished by pushing the screw, pin, wire, rod, bar and/or ring through insertion portions 25, 27, 55, or 57 and into receiving portions 24, 26, 54 or 56 in a direction which may be, for example, perpendicular or oblique to the longitudinal axis 94. Alternatively, the ends of a screw, pin, wire, rod, bar and/or ring may be inserted directly into the receiving portions 24, 26, 54 or 56 and chamfered edges C (FIGS. 1 and 7) may assist in guiding the screw, pin, wire, rod, bar and/or ring into the receiving portions 24, 26, 54 or 56. As the end of a screw, pin, wire, rod, bar and/or ring is pushed against the chamfered edges C, the vise plates 8 and 10 may move apart, thereby allowing the screw, pin, wire, rod, bar and/or ring to be inserted directly into the receiving portions 24, 26, 54 or 56. While not shown, those skilled in the are will appreciate that chamfered edges C may also be incorporated into the vise plates 12 and 14. With the nut 86 is in a loosened condition, the screw, pin, wire, rod, bar and/or ring may be inserted (e.g., clipped or snapped) into the receiving portions 24, 26, 54 and/or 56, the first and second clamp assemblies 2, 4 may be rotated relative to each other, the first vise plate 8 may move towards or away from the second vise plate 10, the second vise plate 10 may move towards or away from the third vise plate 12, and/or the third vise plate 12 may move towards or away from the fourth vise plate 14. Moreover, in the loosened condition, the posts 106 and 108 may move within the receiving openings 110 and 112, respectively, and the posts 114 and 116 may move within the receiving openings 118 and 120. In some embodiments, the movement of the posts 106, 108, 114, 116 within the receiving portions 110, 112, 118, 120 may be rotational and/or translational.

Once the appropriate combination of screw(s), pin(s), wire (s), rod(s), bar(s) and/or ring(s) are inserted into the clamp 1, the nut 86 may be tightened, thereby locking the screw, pin, wire, rod, bar and/or ring within the receiving portions 24, 26, 54, 56 and fixing the first and second clamp assemblies 2 and 4 with respect to each other. For example, as shown in FIG. 7, the rod 136 and wires 138, 150 may be inserted into the clamp 1. The clamp 1 may be adjusted such that the rod 136 and wires 138, 150 may be at an angle relative to each other.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. A clamp for external fixation having a longitudinal axis comprising:
    a longitudinal bore passing through the clamp;
    a first clamp assembly comprising first and second vise plates having two first recesses and two second recesses, respectively, the first vise plate comprising a first contacting surface, the second vise plate comprising a second contacting surface, the first and second contacting surfaces being configured to directly contact one another in a clamping position, the first recesses being positioned and shaped so that, when the first and second vise plates contact one another in the clamping position, first and second bone fixation element receiving cavities are formed on opposite sides of the longitudinal bore, each of the second recesses being adjacent to a corresponding one of the first recesses and shaped so that, when the first and second vise plates are in the clamping position, first and second insertion channels are formed adjacent to the first and second bone fixation element receiving cavities, respectively, each of the first and second insertion channels extending along a channel axis from the corresponding one of the first and second bone fixation element receiving cavities to open to an exterior of the first clamp assembly, the channel axes of the first and second insertion channels being angled with respect to the longitudinal axis;
    a second clamp assembly comprising a third and fourth receiving portions, each of the third and fourth receiving portions being sized and configured to receive a bone fixation element therein; and
    a shaft positioned through the longitudinal bore, the shaft connecting the first and second clamp assemblies.

2. The device of claim 1, wherein the shaft has a head portion and a threaded end portion.

3. The device of claim 2, wherein one of the first and second clamp assemblies has a first opening sized and configured to receive the head portion of the shaft such that the head portion is prevented from rotating with respect to one of the first and second clamp assemblies.

4. The device of claim 2, further comprising a connection device for engaging the threaded end portion of the shaft such that the first and second clamp assemblies are positioned between the connection device and the head portion of the shaft.

5. The device of claim 4, wherein the connection device is a nut.

6. The device of claim 2, wherein one of the first and second clamp assemblies comprises an internal thread for receiving the threaded end portion of the shaft.

7. The device of claim 1, wherein the channel axis is non-perpendicular with respect to the longitudinal axis.

8. The device of claim 1, further comprising a first serrated portion operably associated with the first clamp assembly and a second serrated portion operably associated with the second clamp assembly, wherein the second serrated portion is engagable with the first serrated portion to selectively fix the first clamp assembly with respect to the second clamp assembly.

9. The device of claim 8, further comprising a deformable biasing member between the first and second clamp assemblies biased to move the first and second serrated portions away from one another toward a disengaged position in which the first and second clamp assemblies are rotatable about the longitudinal axis with respect to one another.

10. The device of claim 1, where in the second clamp assembly comprises third and fourth vise plates having two third recesses and two fourth recesses, respectively, the third recesses being positioned and shaped so that, when the third and fourth vise plates contact one another in a clamping position, third and fourth bone fixation element receiving cavities are formed on opposite sides of the longitudinal bore, each of the fourth recesses being adjacent to a corresponding one of the third recesses and shaped so that, when the third and fourth vise plates are in the clamping position, third and fourth insertion channels are formed adjacent to the third and fourth bone fixation element receiving cavities, respectively, each of the third and fourth insertion channels extending along a channel axis from the corresponding one of the third and fourth bone fixation element receiving cavities to open to an exterior of the second clamp assembly, the channel axes of the third and fourth insertion channels being angled with respect to the longitudinal axis.

11. The device of claim 10, further comprising a post operably associated with one of the first, second, third and fourth vise plates.

12. The device of claim 11, further comprising a second opening in one of the first, second, third and fourth vise plates for receiving the post.

13. The device of claim 10, wherein one of the first, second, third and fourth vise plates comprises a sloping surface proximate one of the first, second, third and fourth recesses.

14. The device of claim 13, wherein the second recesses include a surface sloping at an angle between about 20 degrees and about 40 degrees relative to a plane perpendicular to the longitudinal axis.

15. The device of claim 10, wherein one of the first and third recesses is substantially V-shaped.

16. The device of claim 15, wherein the V-shape has an angle between about 110 degrees and about 130 degrees.

* * * * *